US00PP31276P2

(12) United States Plant Patent
Hartman

(10) Patent No.: US PP31,276 P2
(45) Date of Patent: Dec. 24, 2019

(54) ***CALADIUM* PLANT NAMED 'RSL 2321-469'**

(50) Latin Name: ***Caladium* X *hortulanum***
Varietal Denomination: RSL 2321-469

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/350,104

(22) Filed: Sep. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/00
See application file for complete search history.

*Primary Examiner* — June Hwu
(74) *Attorney, Agent, or Firm* — C. A. Whealy

(57) ABSTRACT

A new and distinct cultivar of *Caladium* plant named 'RSL 2321-469', characterized by its intermediate height; upright and mounding plant habit; dense and bushy appearance; vigorous growth habit and rapid growth rate; lance-type leaves that are light green variably flushed with greyed red in color; and petioles that are greyed green in color with darker-colored tessellations.

5 Drawing Sheets

Botanical designation: *Caladium* X *hortulanum*.
Cultivar denomination: 'RSL 2321-469'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'RSL 2321-469'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'Florida Red Ruffles', disclosed in U.S. Plant Pat. No. 13,136, as the female, or seed, parent with *Caladium* X *hortulanum* 'Creamsickle', disclosed in U.S. Plant Pat. No. 23,991, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RSL 2321-469'. These characteristics in combination distinguish 'RSL 2321-469' as a new and distinct *Caladium* plant:

1. Intermediate in height and upright and mounding plant habit; dense and bushy appearance.
2. Vigorous growth habit and rapid growth rate.
3. Lance-type leaves that are light green variably flushed with greyed red in color.
4. Petioles that are greyed green in color with darker-colored tessellations.

Plants of the new *Caladium* differ primarily from plants of the female parent, 'Florida Red Ruffles', in the following characteristics:

1. Plants of the new *Caladium* grow faster than plants of 'Florida Red Ruffles'.
2. Plants of the new *Caladium* and 'Florida Red Ruffles' differ in leaf color as leaves of the new *Caladium* are light green variably flushed with greyed red in color whereas leaves of 'Florida Red Ruffles' have dark red-colored venation and interveinal areas and green-colored borders.
3. Plants of the new *Caladium* and 'Florida Red Ruffles' differ in leaf petiole color as petioles of the new *Caladium* are greyed green in color with darker-colored tessellations whereas petioles of 'Florida Red Ruffles' are black in color with pinkish tan-colored stripes.

Plants of the new *Caladium* differ primarily from plants of the male parent, 'Creamsickle', in the following characteristics:

1. Plants of the new *Caladium* more mounding than and not as upright as plants of 'Creamsickle'.
2. Plants of the new *Caladium* and 'Creamsickle' differ in leaf color as leaves of the new *Caladium* are light green variably flushed with greyed red in color whereas leaves of 'Creamsickle' have greyed green-colored venation and greyed green and greyed purple-colored interveinal areas interspersed with dark green-colored sectors and borders.

Plants of the new *Caladium* can be compared to plants of *Caladium* X *hortulanum* 'Desert Sunset', disclosed in U.S. Plant Pat. No. 25,421. In side-by-side comparisons, plants of the new *Caladium* differ primarily from plants of 'Desert Sunset' in the following characteristics:

1. Plants of the new *Caladium* are denser and bushier than plants of 'Desert Sunset'.
2. Plants of the new *Caladium* and 'Desert Sunset' differ in leaf color as leaves of the new *Caladium* are light green variably flushed with greyed red in color whereas leaves of 'Desert Sunset' are bronze salmon pink in color with darker-colored venation.
3. Plants of the new *Caladium* and 'Desert Sunset' differ in leaf petiole color as petioles of the new *Caladium* are greyed green in color with darker-colored tessellations whereas petioles of 'Desert Sunset' are greenish tan with darker-colored stripes.

Plants of the new *Caladium* can be compared to plants of *Caladium* X *hortulanum* 'Chinook', disclosed in U.S. Plant Pat. No. 27,094. In side-by-side comparisons, plants of the new *Caladium* differ primarily from plants of 'Chinook' in the following characteristics:

1. Plants of the new *Caladium* and 'Chinook' differ in leaf color as leaves of the new *Caladium* are light green variably flushed with greyed red in color whereas leaves of 'Chinook' are medium green in color flushed with salmon pink and dark pink-colored venation.
2. Plants of the new *Caladium* and 'Chinook' differ in leaf petiole color as petioles of the new *Caladium* are greyed green in color with darker-colored tessellations whereas petioles of 'Chinook' are greenish tan tinged with pink and with darker greenish brown-colored streaks, stipples and stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'RSL 2321-469' in a container and grown in a shadehouse (tuber de-eyed).

The photograph on the second sheet is a side perspective view of a typical plant of 'RSL 2321-469' in a container and grown in a shadehouse (tuber not de-eyed).

The photograph at the top of the third sheet is a comparison view of typical potted plants of the female parent, 'Florida Red Ruffles' (left), 'RSL 2321-469' (center) and the male parent, 'Creamsickle' (right).

The photograph at the bottom of the third sheet is a comparison view of typical potted plants of 'Desert Sunset' (left), 'RSL 2321-469' (center) and 'Chinook' (right).

The photograph at the top of the fourth sheet is a comparison view of typical plants of 'RSL 2321-469' grown in containers; the plant on the left has not had its tuber de-eyed and the plant on the right has had its tuber de-eyed prior to planting.

The photograph at the bottom of the fourth sheet is a close-up view of typical freshly-harvested tubers with roots and leaf petioles of 'RSL 2321-469'.

The photograph on the fifth sheet is a side perspective view of typical plants of 'RSL 2321-469' grown in an open production field.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were 7.5 months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'RSL 2321-469'.

Parentage:

*Female, or seed, parent.*—*Caladium* X *hortulanum* 'Florida Red Ruffles', disclosed in U.S. Plant Pat. No. 13,136.

*Male, or pollen, parent.*—*Caladium* X *hortulanum* 'Creamsickle', disclosed in U.S. Plant Pat. No. 23,991.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular in shape. Height: About 4.3 cm. Diameter: About 4.9 cm to 8.4 cm. Segment height: About 2.3 cm to 3 cm. Segment diameter: About 2 cm to 3.2 cm. Axillary bud size: About 5 mm by 5 mm. Texture: Thick, starchy; somewhat brittle. Color: Epidermis, freshly-harvested: Close to 158D. Epidermis, dried: Close to 200A. Cortical tissue: Close to 155B and 1D. Axillary buds: Close to N155C and N155D. Root description: Thick, fleshy contractile roots with few lateral branches; color, close to 155C. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Intermediate in height and upright to mounded plant habit; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants.*—About 29 cm to 33 cm.

*Plant diameter or spread, shadehouse-grown potted plants.*—About 34 cm to 45 cm.

*Number of shoots per plant, shadehouse-grown potted plants, tubers not de-eyed.*—About three to four develop per #1 tuber.

*Number of shoots per plant, shadehouse-grown potted plants, tubers de-eyed.*—About four to six develop per #1 tuber.

*Cataphylls, shadehouse-grown potted plants.*—Length: About 5 cm to 12.7 cm. Width: About 1 cm to 1.4 cm. Shape: Wedge-shaped or elongated elliptic. Apex: Acute to acuminate. Base: Sheathing the stem. Color, inner surface: Close to N155D; colors and patterns on the outer surface are visible on the inner surface. Color, outer surface: Close to N170D and 36D densely streaked and stippled with close to 147A; with development, color becoming closer to N199D.

Leaf description:

*Arrangement and type.*—Alternate; simple; lance-type.

*Length, shadehouse-grown potted plants.*—About 16.5 cm to 23 cm.

*Width, shadehouse-grown potted plants.*—About 8.5 cm to 12 cm; when flattened, about 10 cm to 13.2 cm.

*Shape.*—Ovate to lanceolate.

*Apex.*—Acuminate.

*Base.*—Sagittate to peltate.

*Margin.*—Entire; wavy with broad undulations.

*Texture and luster, upper and lower surfaces.*—Smooth, glabrous; dull sheen.

*Venation pattern.*—Pinnate.

*Color, shadehouse-grown potted plants.*—Developing and fully developed leaves, upper surface: Background color: Close to 147D and 146D variably and heavily flushed with close to 181B, 181C and 181D; with development, colored sectors becoming closer to 147B, between 147B to 146B and 146A and/or variably mottled and flushed with close to 178A, 178B, 181B, 183B tinged with close to 177B. Towards the margins: Close to 147B to 147C flushed with close to 181C. Leaf edge: Close to 183A; with development, color becoming closer to 183A to 183B. Basal notch: Close to 185A; with development, color becoming closer to 183A and 187A. Leaf attachment point: Close to 183A. Midvein: Close to 194A flushed with close to 178A with streaks and flecks, close to 181A; with development, color becoming closer to 159C to 159D with flecks and streaks, close to 183A tinged with close to 177A, surrounding the midvein, close to 183A. Primary venation: Close to 178A surrounded by close to 181A; with development, color becoming closer to 147A and 147B tinged with close to 146B variably flushed with close to 183A tinged with close to 177A and/or close to 187A tinged with close to 177A. Interveinal areas: Close to 147D and 146D variably and heavily flushed with close to 181B, 181C and 181D; with development, colored sectors becoming closer to 147B, between 147B to 146B and 146A and/or variably mottled and flushed with close to 178A, 178B, 181B, 183B tinged with close to 177B. Developing and fully developed leaves, lower surface: Background color: Close to 194A and 194B; with development, close to 147B to 147C tinged with close to 182B to 182C. Leaf edge: Close to 183A to 183B. Basal notch: Close to 183A. Leaf attachment point: Close to 187C to 187D. Midvein: Close to 194B. Primary venation: Close to 147C to 147D. Interveinal areas: Close to 194A and 194B; with development, close to 147B to 147C tinged with close to 182B to 182C.

*Petioles.*—Aspect: Initially upright and straight and outwardly leaning with development; flexible. Length, shadehouse-grown potted plants: About 18 cm to 30.4 cm. Diameter, distally, shadehouse-grown potted plants: About 2.5 mm to 4 mm. Diameter, proximally, shadehouse-grown potted plants: About 6 mm to 8 mm. Texture: Smooth, glabrous; distally, glaucous. Color, shadehouse-grown potted plants: When developing and fully developed: Close to 195A, 195B and 159C tinged with close to N170D with faint stipples, streaks and tessellations of close to 147B and 147C tinged with close to 199B. Wing length, shadehouse-grown potted plants: About 4.7 cm to 5.5 cm. Wing diameter, shadehouse-grown potted plants: About 8 mm. Texture and luster, inner and outer surfaces: Smooth, glabrous; dull. Wing color, shadehouse-grown potted plants: Inner surface: Close to N155D; colors and patterns on the outer surface are visible on the inner surface. Outer surface: Close to 159C, stippled, streaked and tessellated with close to 147B.

Inflorescence description: To date, inflorescence development has not been observed on plants of the new *Caladium.*

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RSL 2321-469' as illustrated and described.

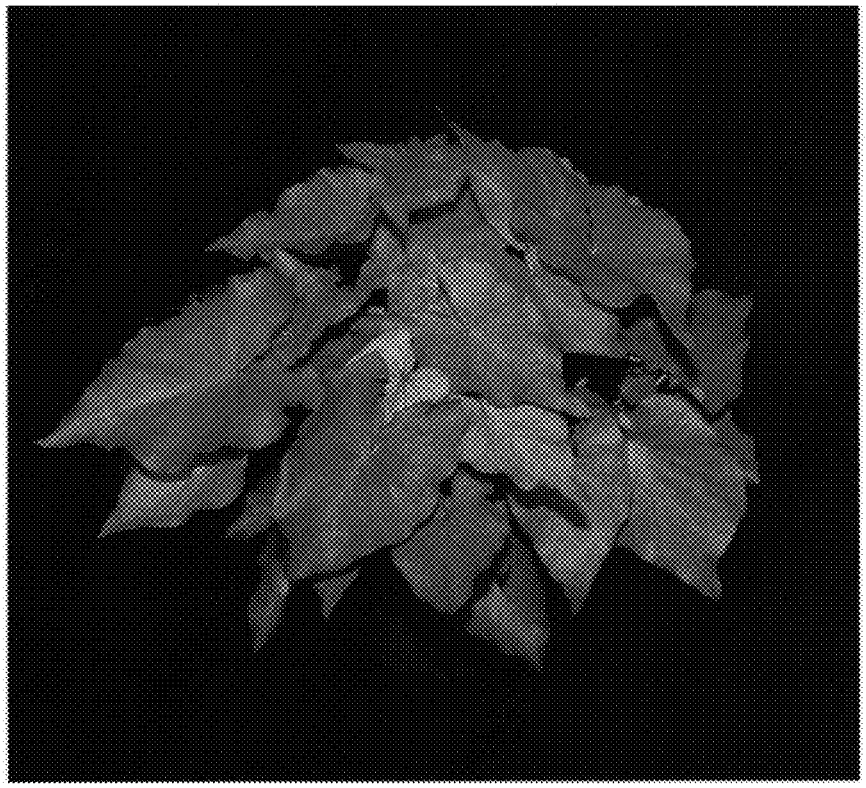

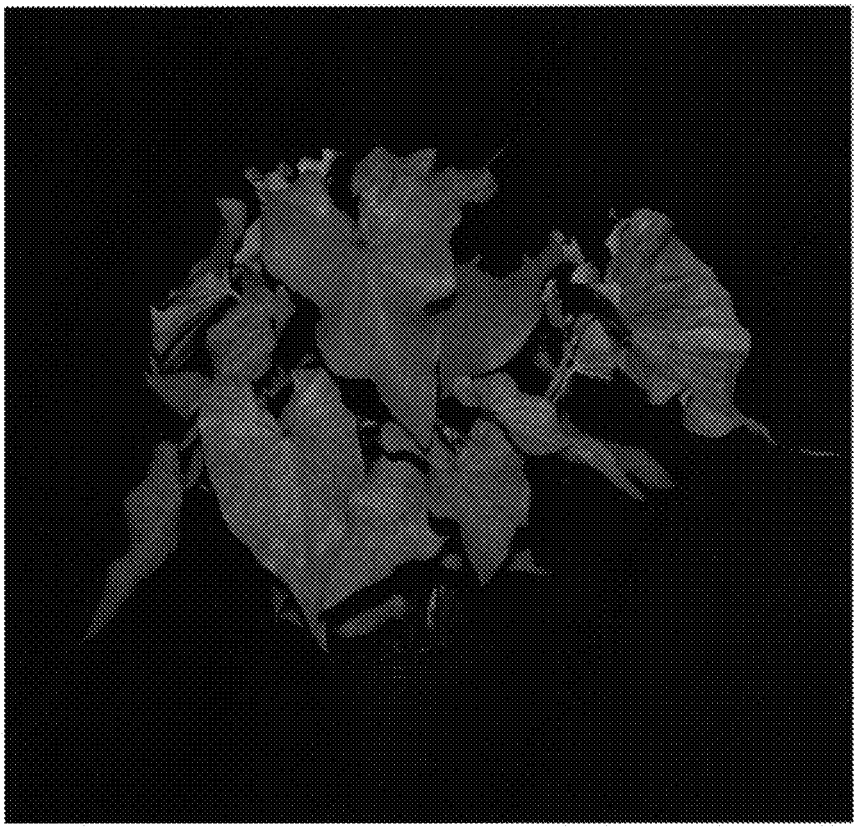

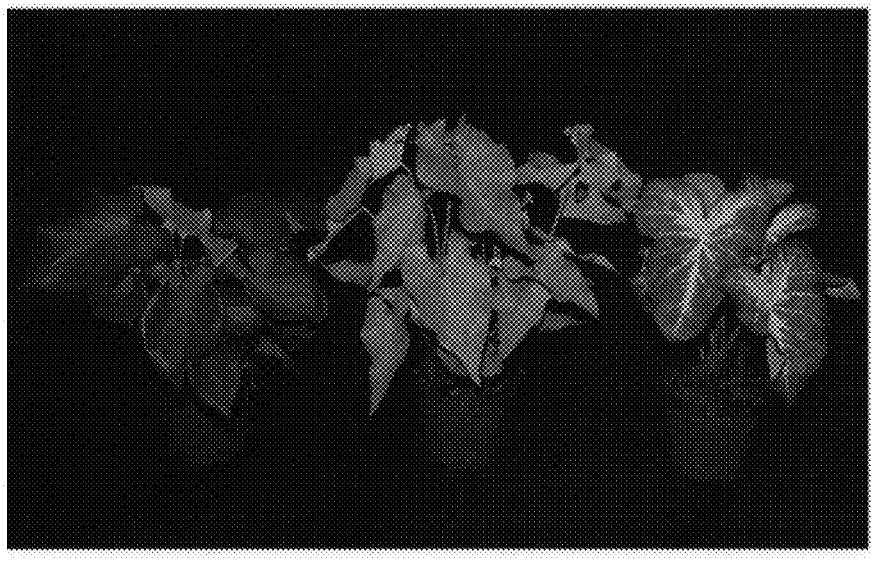
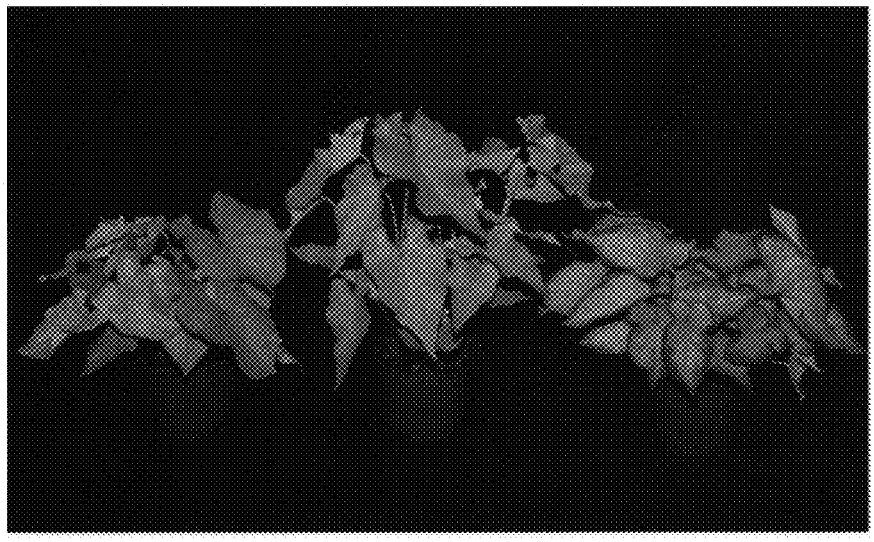

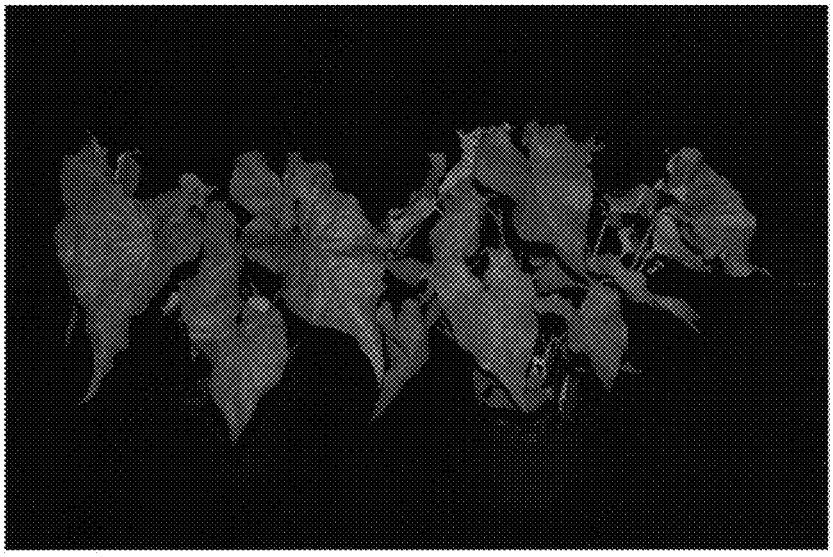
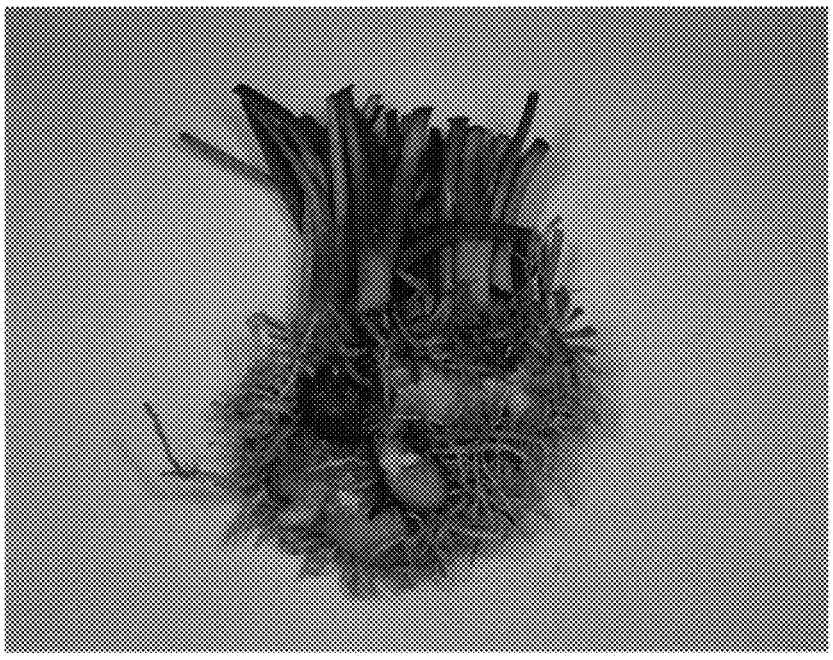

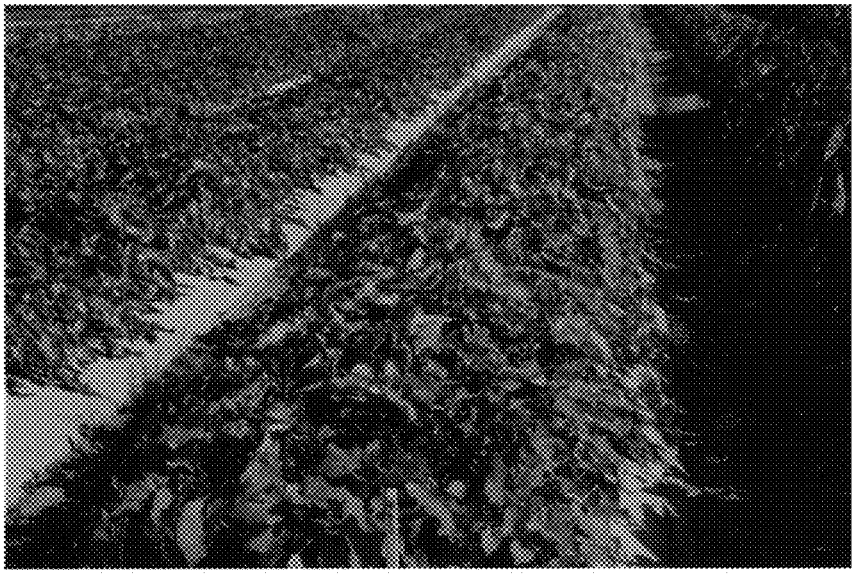

* * * * *